United States Patent
Smith et al.

(10) Patent No.: US 9,339,318 B2
(45) Date of Patent: May 17, 2016

(54) METHOD AND APPARATUS FOR PREPARING A PROXIMAL FEMUR

(71) Applicant: Biomet Manufacturing, LLC, Warsaw, IN (US)

(72) Inventors: Aaron P. Smith, Warsaw, IN (US); Eric J. Fontenot, Warsaw, IN (US); Tyler D. Witt, Warsaw, IN (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 52 days.

(21) Appl. No.: 14/020,985

(22) Filed: Sep. 9, 2013

(65) Prior Publication Data

US 2014/0012268 A1   Jan. 9, 2014

Related U.S. Application Data

(63) Continuation of application No. 12/718,026, filed on Mar. 5, 2010, now Pat. No. 8,529,569.

(51) Int. Cl.
| | | |
|---|---|---|
| *A61B 17/00* | (2006.01) | |
| *A61B 17/88* | (2006.01) | |
| *A61B 17/56* | (2006.01) | |
| *A61F 2/36* | (2006.01) | |

(52) U.S. Cl.
CPC .................. *A61B 17/88* (2013.01); *A61B 17/00* (2013.01); *A61B 17/56* (2013.01); *A61F 2/3601* (2013.01)

(58) Field of Classification Search
CPC . A61F 2/3601; A61F 2/3607; A61F 2/30728; A61F 2/4607; A61B 17/154; A61B 17/155
USPC ............. 606/79–85, 86 R–91, 96; 623/20.35, 623/20.36, 23.15–23.38, 22.12
See application file for complete search history.

(56) References Cited

U.S. PATENT DOCUMENTS

| | | | |
|---|---|---|---|
| 2,231,864 A | | 2/1941 | Abel |
| 3,815,599 A | | 6/1974 | Deyerle |
| 4,012,796 A | * | 3/1977 | Weisman et al. .......... 623/23.28 |
| 4,306,550 A | | 12/1981 | Forte |
| 4,535,487 A | * | 8/1985 | Esper et al. ................ 623/23.29 |
| 4,549,319 A | | 10/1985 | Meyer |

(Continued)

FOREIGN PATENT DOCUMENTS

| | | |
|---|---|---|
| DE | 29516473 U1 | 12/1995 |
| EP | 0453695 A1 | 10/1991 |
| FR | 2676172 A1 | 11/1992 |
| FR | 2732891 A1 | 10/1996 |
| FR | 2792822 A1 | 11/2000 |
| GB | 2299758 A | 10/1996 |
| WO | WO-94/21199 A1 | 9/1994 |
| WO | WO-2007106752 A2 | 9/2007 |

OTHER PUBLICATIONS

DePuy, a Johnson & Johnson company, "REEF: Distally Interlocked Modular Femoral Reconstruction Prosthesis", 2004, 7 sheets.
Zimmer, Inc., "ZMR Hip System", 2004, 19sheets.

*Primary Examiner* — Kevin T Truong
*Assistant Examiner* — Si Ming Ku
(74) *Attorney, Agent, or Firm* — Schwegman Lundberg & Woessner, P.A.

(57) ABSTRACT

A system for preparing a proximal femur can include a broach that includes a broach body having an anterior side, a posterior side, a lateral side and a medial side. The medial side can have a roughened cutting surface. The lateral side can have a smooth, non-cutting surface. The system can further comprise a cutting scribe assembly and a cutting guide assembly.

16 Claims, 17 Drawing Sheets

(56) References Cited

U.S. PATENT DOCUMENTS

| | | | |
|---|---|---|---|
| 4,552,136 A | 11/1985 | Kenna | |
| 4,601,289 A | 7/1986 | Chiarizzio et al. | |
| 4,718,915 A | 1/1988 | Epinette | |
| 4,728,333 A | 3/1988 | Masse et al. | |
| 4,770,660 A * | 9/1988 | Averill | 623/23.22 |
| 4,790,852 A | 12/1988 | Noiles | |
| 4,842,606 A | 6/1989 | Kranz et al. | |
| 4,883,492 A | 11/1989 | Frey et al. | |
| 4,904,269 A | 2/1990 | Elloy et al. | |
| 4,959,066 A | 9/1990 | Dunn et al. | |
| 5,041,118 A | 8/1991 | Wasilewski | |
| 5,047,035 A | 9/1991 | Mikhail et al. | |
| 5,061,271 A | 10/1991 | Van Zile | |
| 5,080,685 A | 1/1992 | Bolesky et al. | |
| 5,089,004 A | 2/1992 | Averill et al. | |
| 5,092,900 A | 3/1992 | Marchetti et al. | |
| 5,122,146 A | 6/1992 | Chapman et al. | |
| 5,201,769 A | 4/1993 | Schutzer | |
| 5,211,666 A | 5/1993 | Fetto | |
| 5,376,124 A * | 12/1994 | Gustke et al. | 623/23.28 |
| 5,409,492 A | 4/1995 | Jones et al. | |
| 5,468,243 A | 11/1995 | Halpern | |
| 5,489,284 A | 2/1996 | James et al. | |
| 5,562,666 A | 10/1996 | Brumfield | |
| 5,571,111 A | 11/1996 | Aboczky | |
| 5,578,037 A | 11/1996 | Sanders et al. | |
| 5,601,564 A | 2/1997 | Gustilo et al. | |
| 5,607,431 A | 3/1997 | Dudasik et al. | |
| 5,624,445 A | 4/1997 | Burke | |
| 5,632,747 A | 5/1997 | Scarborough et al. | |
| 5,645,549 A | 7/1997 | Boyd et al. | |
| 5,649,930 A | 7/1997 | Kertzner | |
| 5,665,090 A | 9/1997 | Rockwood et al. | |
| 5,683,470 A | 11/1997 | Johnson et al. | |
| 5,690,636 A | 11/1997 | Wildgoose et al. | |
| 5,699,915 A | 12/1997 | Berger et al. | |
| 5,704,940 A | 1/1998 | Garosi | |
| 5,766,261 A | 6/1998 | Neal et al. | |
| 5,766,262 A * | 6/1998 | Mikhail | 623/23.25 |
| 5,776,194 A | 7/1998 | Mikol et al. | |
| 5,788,701 A | 8/1998 | McCue | |
| 5,849,015 A | 12/1998 | Haywood et al. | |
| 5,860,969 A | 1/1999 | White et al. | |
| 5,860,982 A | 1/1999 | Ro et al. | |
| 5,908,423 A | 6/1999 | Kashuba et al. | |
| 5,913,860 A | 6/1999 | Scholl | |
| 5,976,145 A | 11/1999 | Kennefick, III | |
| 5,989,261 A | 11/1999 | Walker et al. | |
| 6,022,357 A | 2/2000 | Reu et al. | |
| 6,027,505 A | 2/2000 | Peter et al. | |
| 6,033,405 A | 3/2000 | Winslow et al. | |
| 6,066,173 A | 5/2000 | McKernan et al. | |
| 6,110,179 A | 8/2000 | Flivik et al. | |
| 6,110,211 A | 8/2000 | Weiss | |
| 6,113,604 A | 9/2000 | Whittaker et al. | |
| 6,117,138 A * | 9/2000 | Burrows et al. | 606/80 |
| 6,117,173 A | 9/2000 | Taddia et al. | |
| 6,126,694 A | 10/2000 | Gray, Jr. | |
| 6,136,035 A | 10/2000 | Lob et al. | |
| 6,139,551 A | 10/2000 | Michelson et al. | |
| 6,143,030 A | 11/2000 | Schroder | |
| 6,152,963 A | 11/2000 | Noiles et al. | |
| RE37,005 E | 12/2000 | Michelson et al. | |
| 6,159,216 A | 12/2000 | Burkinshaw et al. | |
| 6,206,884 B1 | 3/2001 | Masini | |
| 6,224,605 B1 | 5/2001 | Anderson et al. | |
| 6,224,609 B1 | 5/2001 | Ressemann et al. | |
| 6,238,435 B1 | 5/2001 | Meulink et al. | |
| 6,245,111 B1 | 6/2001 | Shaffner | |
| 6,267,785 B1 | 7/2001 | Masini | |
| 6,302,890 B1 | 10/2001 | Leone, Jr. | |
| 6,306,174 B1 | 10/2001 | Gie et al. | |
| 6,325,804 B1 | 12/2001 | Wenstrom, Jr. et al. | |
| 6,330,845 B1 | 12/2001 | Meulink | |
| 6,338,734 B1 | 1/2002 | Burke et al. | |
| 6,344,060 B1 | 2/2002 | Schmotzer et al. | |
| 6,361,565 B1 | 3/2002 | Bonutti | |
| 6,371,991 B1 | 4/2002 | Manasas et al. | |
| 6,379,384 B1 | 4/2002 | McKernan et al. | |
| 6,395,004 B1 | 5/2002 | Dye et al. | |
| 6,468,281 B1 | 10/2002 | Badorf et al. | |
| 6,517,581 B2 | 2/2003 | Blamey | |
| 6,626,913 B1 | 9/2003 | McKinnon et al. | |
| 6,871,549 B2 | 3/2005 | Serra et al. | |
| 6,875,239 B2 | 4/2005 | Gerbec et al. | |
| 6,883,217 B2 | 4/2005 | Barrette et al. | |
| 6,913,623 B1 | 7/2005 | Zhu | |
| 6,932,819 B2 | 8/2005 | Wahl et al. | |
| 7,074,224 B2 | 7/2006 | Daniels et al. | |
| 7,179,259 B1 | 2/2007 | Gibbs | |
| 7,210,881 B2 | 5/2007 | Greenberg | |
| 7,247,171 B2 | 7/2007 | Sotereanos | |
| 7,255,716 B2 | 8/2007 | Pubols et al. | |
| 7,261,741 B2 * | 8/2007 | Weissman et al. | 623/23.22 |
| 7,291,176 B2 | 11/2007 | Serra et al. | |
| 7,297,166 B2 | 11/2007 | Dwyer et al. | |
| 7,341,589 B2 | 3/2008 | Weaver et al. | |
| 7,425,214 B1 | 9/2008 | McCarthy et al. | |
| 7,491,242 B2 | 2/2009 | Pichon et al. | |
| 7,582,092 B2 | 9/2009 | Jones et al. | |
| 7,585,301 B2 | 9/2009 | Santarella et al. | |
| 7,585,329 B2 | 9/2009 | McCleary et al. | |
| 7,832,405 B1 | 11/2010 | Schlueter et al. | |
| 7,857,858 B2 | 12/2010 | Justin et al. | |
| 7,887,539 B2 | 2/2011 | Dunbar, Jr. et al. | |
| 8,118,868 B2 | 2/2012 | May et al. | |
| 8,221,432 B2 | 7/2012 | Smith et al. | |
| 8,226,725 B2 | 7/2012 | Ferko | |
| 8,333,807 B2 | 12/2012 | Smith et al. | |
| 8,419,743 B2 | 4/2013 | Smith et al. | |
| 8,460,393 B2 | 6/2013 | Smith et al. | |
| 8,529,569 B2 | 9/2013 | Smith et al. | |
| 2003/0233100 A1 | 12/2003 | Santarella et al. | |
| 2004/0107001 A1 | 6/2004 | Cheal et al. | |
| 2004/0122439 A1 | 6/2004 | Dwyer et al. | |
| 2004/0236341 A1 | 11/2004 | Petersen | |
| 2005/0149042 A1 | 7/2005 | Metzger | |
| 2005/0203539 A1 | 9/2005 | Grimm et al. | |
| 2005/0234463 A1 | 10/2005 | Hershberger et al. | |
| 2006/0004459 A1 | 1/2006 | Hazebrouck et al. | |
| 2007/0093844 A1 | 4/2007 | Dye | |
| 2007/0123908 A1 | 5/2007 | Jones et al. | |
| 2007/0129809 A1 | 6/2007 | Meridew et al. | |
| 2007/0233127 A1 | 10/2007 | Tuke et al. | |
| 2008/0125867 A1 | 5/2008 | McCleary et al. | |
| 2008/0154276 A1 | 6/2008 | Pubols et al. | |
| 2008/0161811 A1 | 7/2008 | Daniels et al. | |
| 2008/0208203 A1 | 8/2008 | Moindreau et al. | |
| 2008/0234685 A1 | 9/2008 | Gjerde | |
| 2008/0269765 A1 | 10/2008 | Banerjee et al. | |
| 2008/0281428 A1 | 11/2008 | Meyers et al. | |
| 2008/0294168 A1 | 11/2008 | Wieland | |
| 2009/0099566 A1 | 4/2009 | Maness et al. | |
| 2009/0112218 A1 | 4/2009 | McCleary et al. | |
| 2009/0265014 A1 | 10/2009 | May et al. | |
| 2009/0270866 A1 | 10/2009 | Poncet | |
| 2011/0015634 A1 | 1/2011 | Smith et al. | |
| 2011/0046745 A1 | 2/2011 | Daniels et al. | |
| 2011/0218583 A1 | 9/2011 | Smith et al. | |
| 2011/0218636 A1 | 9/2011 | Smith et al. | |
| 2012/0226282 A1 | 9/2012 | Smith et al. | |
| 2013/0110185 A1 | 5/2013 | Smith et al. | |
| 2013/0231674 A1 | 9/2013 | Smith et al. | |
| 2013/0274889 A1 | 10/2013 | Smith et al. | |
| 2014/0200619 A1 | 7/2014 | Smith et al. | |

\* cited by examiner

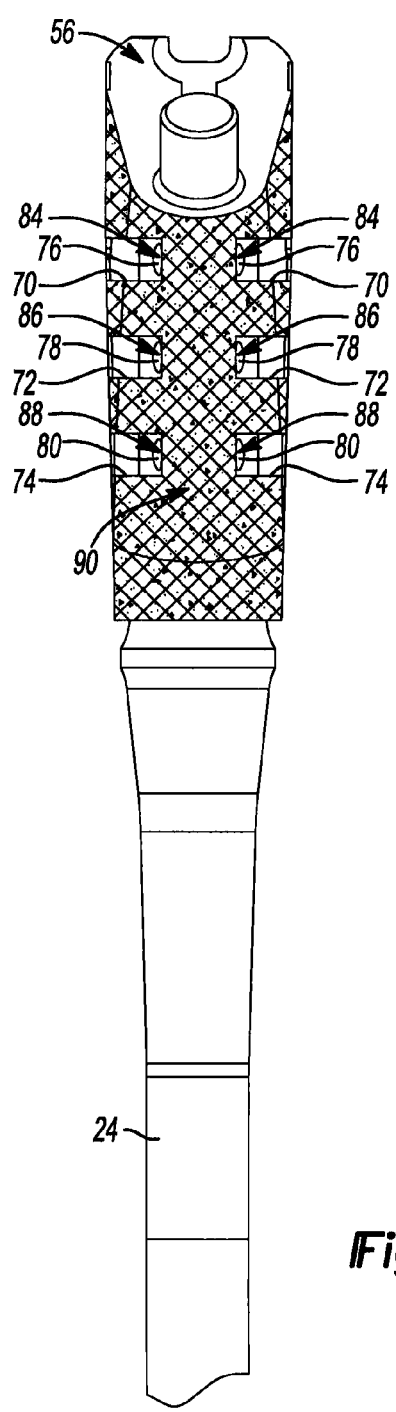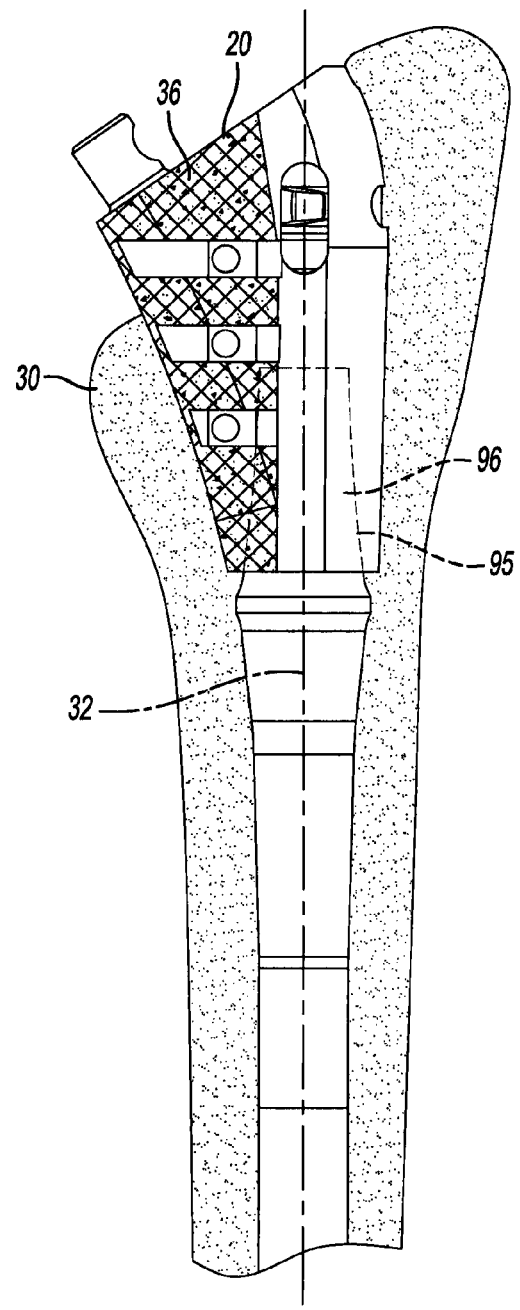
Fig-3
Fig-4

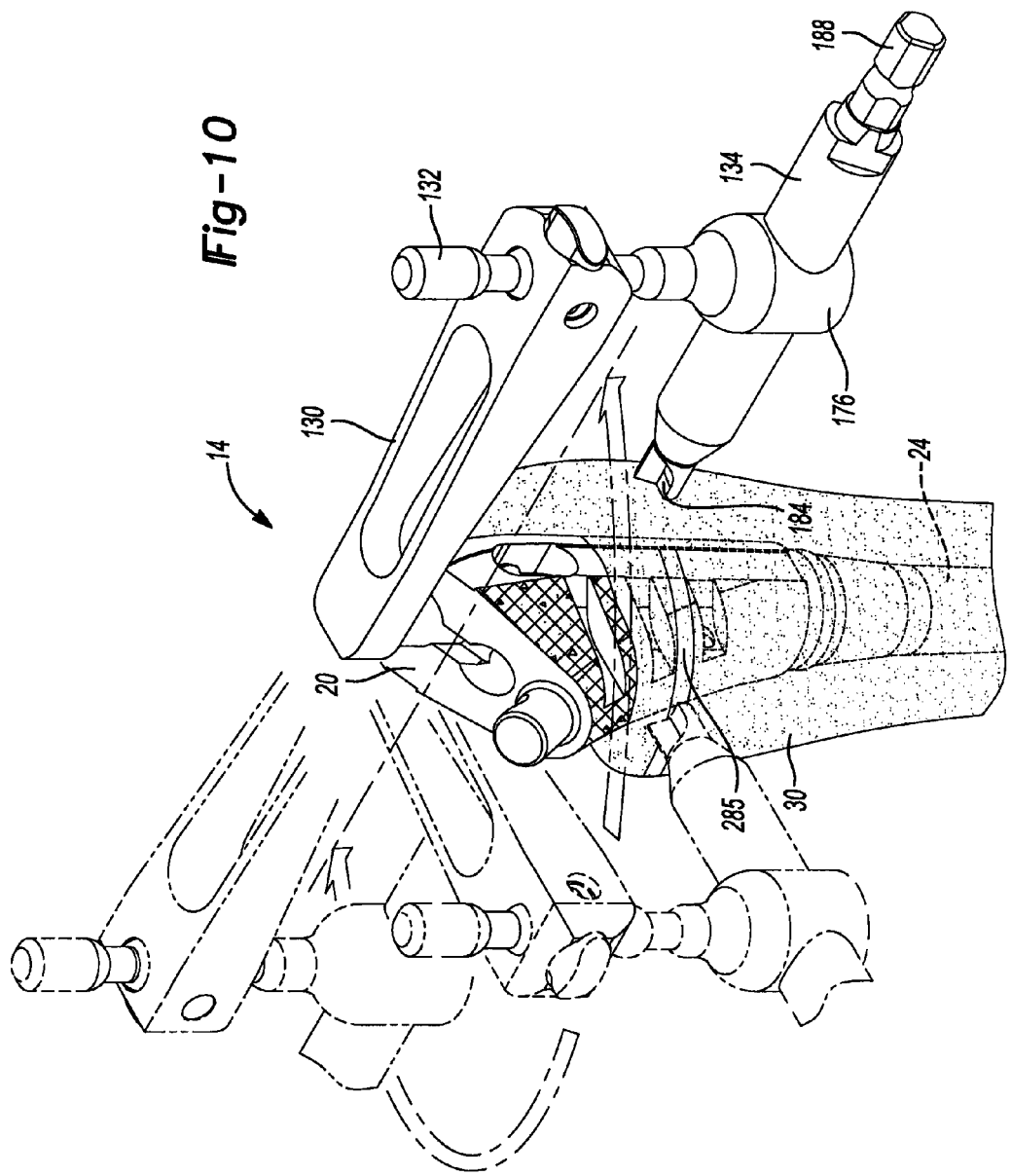

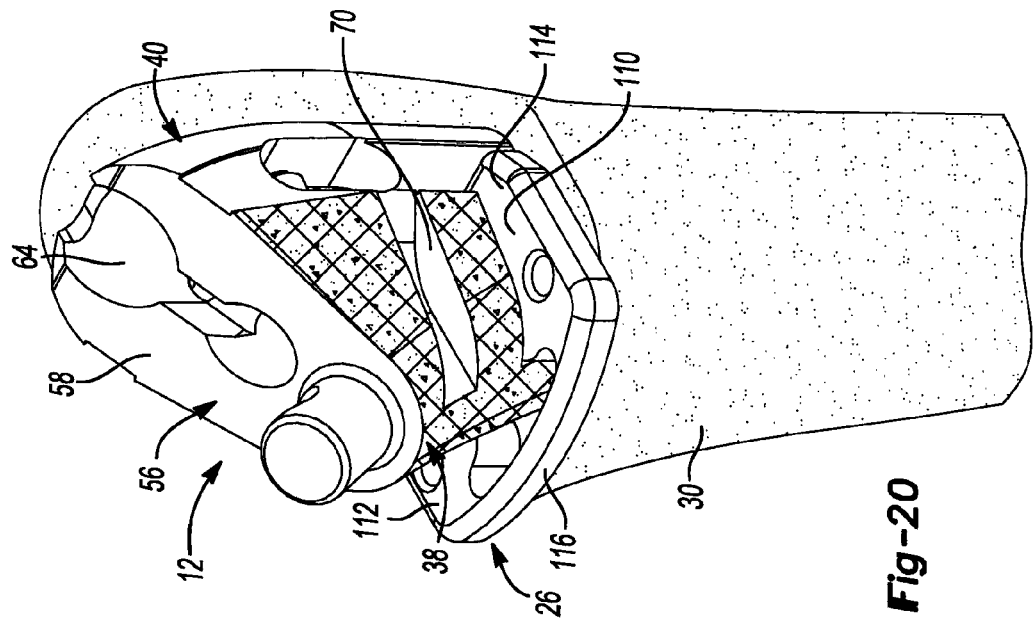
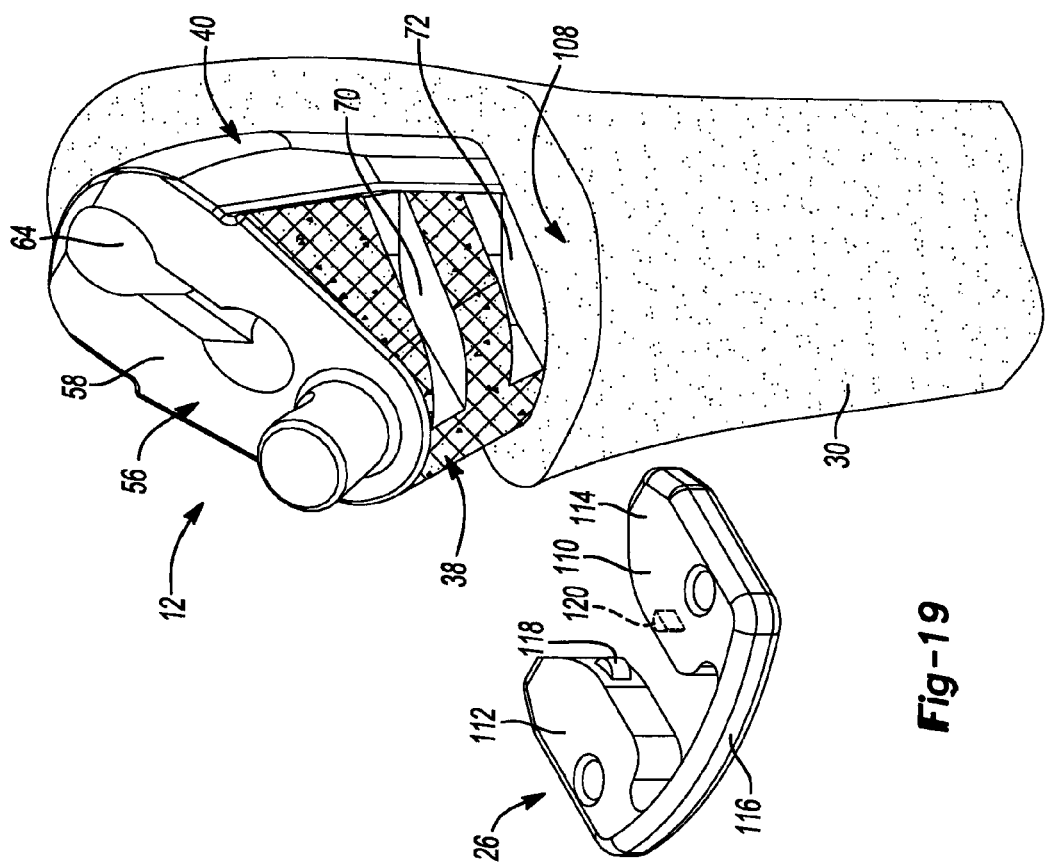

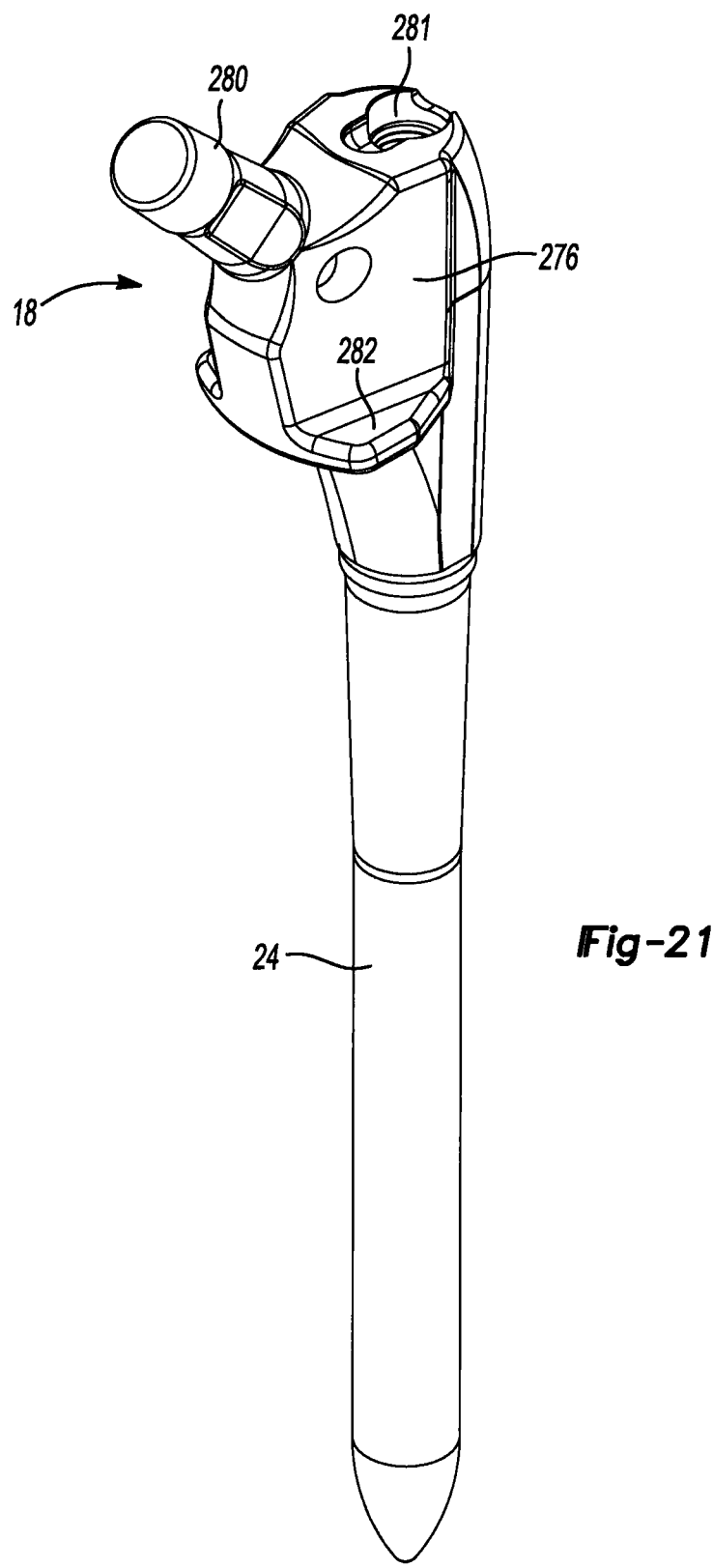

METHOD AND APPARATUS FOR PREPARING A PROXIMAL FEMUR

CROSS-REFERENCE TO RELATED APPLICATIONS

This application is a continuation of U.S. patent application Ser. No. 12/718,026 filed on Mar. 5, 2010, now U.S. Pat. No. 8,529,569.

This application is also related to U.S. patent application Ser. No. 12/718,018 (now U.S. Pat. No. 8,221,432), entitled "METHOD AND APPARATUS FOR IMPLANTING A MODULAR FEMORAL HIP;" U.S. patent application Ser. No. 12/718,230, entitled "MODULAR LATERAL HIP AUGMENTS;" U.S. patent application Ser. No. 12/718,023, entitled "GUIDE ASSEMBLY FOR LATERAL IMPLANTS AND ASSOCIATED METHODS;" U.S. patent application Ser. No. 12/718,027, entitled "ASSEMBLY TOOL FOR MODULAR IMPLANTS AND ASSOCIATED METHOD;" and U.S. patent application Ser. No. 12/718,031, entitled "METHOD AND APPARATUS FOR TRIALING AND IMPLANTING A MODULAR FEMORAL HIP;" each filed on Mar. 5, 2010. The disclosures of each of the above applications are incorporated herein by reference.

FIELD

The present disclosure relates to methods and apparatuses for preparing a proximal femur, such as during a revision procedure.

BACKGROUND

This section provides background information related to the present disclosure which is not necessarily prior art.

Proximal femoral revision surgery can require shaping of weak and/or compromised host femoral bone to accept a new revision implant. Sometimes, preparing the proximal femur, such as with reaming and/or cutting can result in fracture of the proximal femur. In view of this, machining of the femoral canal, such as with reamers is preferable in some instances as compared to impacting broaches.

In some instances, it is desirable to mark a preferred resection level of the proximal femur for receipt of the revision femoral prosthesis. In many examples however, it is difficult to accurately locate a cutting tool relative to the host femur in an effort to identify the preferred level of resection when it is desired to discard deficient bone.

SUMMARY

This section provides a general summary of the disclosure, and is not a comprehensive disclosure of its full scope or all of its features.

A broach for use with a proximal femur can include a broach body having an anterior side, a posterior side, a lateral side and a medial side. The medial side can have a roughened cutting surface. The lateral side can have a smooth, non-cutting surface.

According to additional features, the roughened cutting surface comprises ground cutting teeth. The broach can include at least one notch formed generally transverse to a longitudinal axis of the broach. The notch can be configured for removably receiving a shelf insert. In one example, three notches can be formed at distinct elevations along the longitudinal axis of the broach. Each notch can be configured to selectively receive the shelf insert.

In one example, the broach assembly can include the broach body and the shelf insert that is removably located at the notch. The anterior side of the broach body can have both of a partially roughened cutting surface and a partially smooth, non-cutting surface. The posterior side of the broach body can have both of a partially roughened cutting surface and a partially smooth non-cutting surface.

In one example, the notch can be formed solely on the roughened cutting surface. In one example, each notch can be collectively defined by a pair of disconnected notches. The pair of disconnected notches can comprise an anterior notch and a posterior notch, respectively formed at the same elevation on the longitudinal axis of the broach.

The shelf insert can include a generally U-shaped body and include a first finger that selectively locates into the anterior notch and a second finger that selectively locates into the posterior notch and an intermediate connecting portion that locates around the medial side of the broach body in an assembled position.

According to additional features, the broach assembly can further comprise the broach body and a cutting scribe assembly. The broach body can include a locating bore provided on a superior surface. The cutting scribe assembly can include an arm, a connecting link and a cutting tool. The arm can have a first end that includes a locating boss and a second end that includes the connecting link. The locating boss can selectively locate into the locating bore of the broach body. The cutting tool can be movably coupled to the connecting link. The cutting tool can extend along a cutting axis that is substantially parallel to a longitudinal axis defined by the arm. The cutting scribe assembly can selectively rotate about an axis defined by the locating boss, such that the cutting tool is operable to mark or score the proximal femur to identify a desired cutting area.

According to still other features, the broach assembly can include the broach body and the cutting guide assembly. The broach body can include a locating bore provided on a superior surface. The cutting guide assembly can comprise an arm, a connecting link and a cutting block. The arm can have a first end that includes a locating boss and a second end that includes a connecting link. The locating boss can be selectively located into the locating bore of the broach body. The cutting block can be movably coupled to the connecting link. The cutting block can have cutting slots formed therein. The cutting slots can include a first cutting slot that extends in a direction substantially parallel to the longitudinal axis of the broach and another cutting slot that extends in a direction substantially transverse to the longitudinal axis of the broach.

A method for preparing a proximal femur can include advancing a broach along an opening in the proximal femur. The broach can have a roughened cutting surface on a medial side and a smooth, non-cutting surface on the lateral side. Host bone can be removed with the cutting surface during the advancing. A cutting scribe assembly can be connected to the broach. The cutting scribe assembly can be rotated around a longitudinal axis of the broach. A surface of the proximal femur can be marked or scored with a cutting tool of the cutting scribe assembly. The broach and cutting scribe assembly can then be removed. The proximal femur can be cut at the scored surface. In one example, connecting the cutting scribe assembly to the broach can comprise locating a boss extending from an arm of the cutting assembly into a bore provided on a superior surface of the broach. Locating the boss can include magnetically coupling the boss to the bore. The magnetic coupling can provide magnetic attraction between the boss and the bore while still permitting rotation of the boss within the bore.

The method can further comprise adjusting a connecting link between the arm and the cutting tool to attain a desired alignment with the cutting tool and the proximal femur. The adjusting can comprise advancing the connecting link in a direction parallel to the longitudinal axis of the broach. The method can further comprise advancing the cutting tool in a direction transverse to the longitudinal axis of the broach through an aperture in the connecting link.

According to other features, the method can further include removably attaching a shelf insert to the broach. The shelf insert can extend along a plane that is substantially perpendicular to the longitudinal axis of the broach. The broach can be advanced back into the opening in the proximal femur until the shelf insert engages a calcar shelf of the proximal femur. The position of the broach can then be evaluated.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a medial view of the first broach and stem of FIG. 2;

FIG. 4 is an anterior view of a left femur shown with the first broach and stem cooperating with the IM canal of the femur during use;

FIG. 10 is an anterior perspective view of an exemplary left proximal femur shown with the scribe assembly cooperating with the first broach during an exemplary scribing technique;

FIG. 19 is an exploded perspective view of a shelf insert and the first broach with the first broach locating into an IM canal of an exemplary left proximal femur;

FIG. 20 is an anterior perspective view of the first broach shown with the shelf insert in an assembled position and with the first broach located into an IM canal of the exemplary left proximal femur;

FIG. 21 is an anterior perspective view of an exemplary proximal femoral implant according to the present teachings.

Corresponding reference numerals indicate corresponding parts throughout the several views of the drawings.

DETAILED DESCRIPTION

Example embodiments will now be described more fully with reference to the accompanying drawings.

Figure 1:
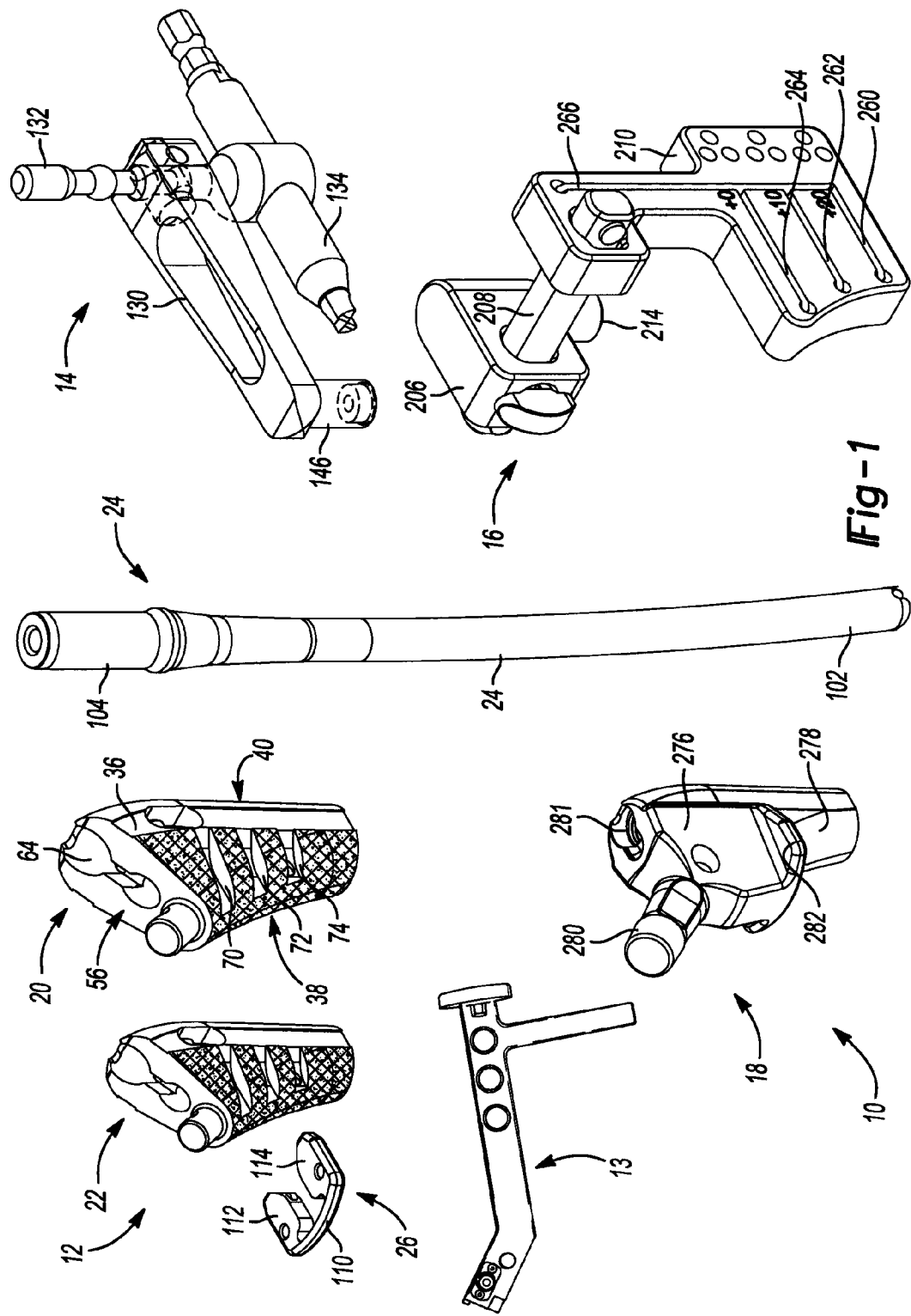
FIG. 1 is a perspective view of a revision system for preparing a proximal femur according to various features of the present teachings.
Figure 2:
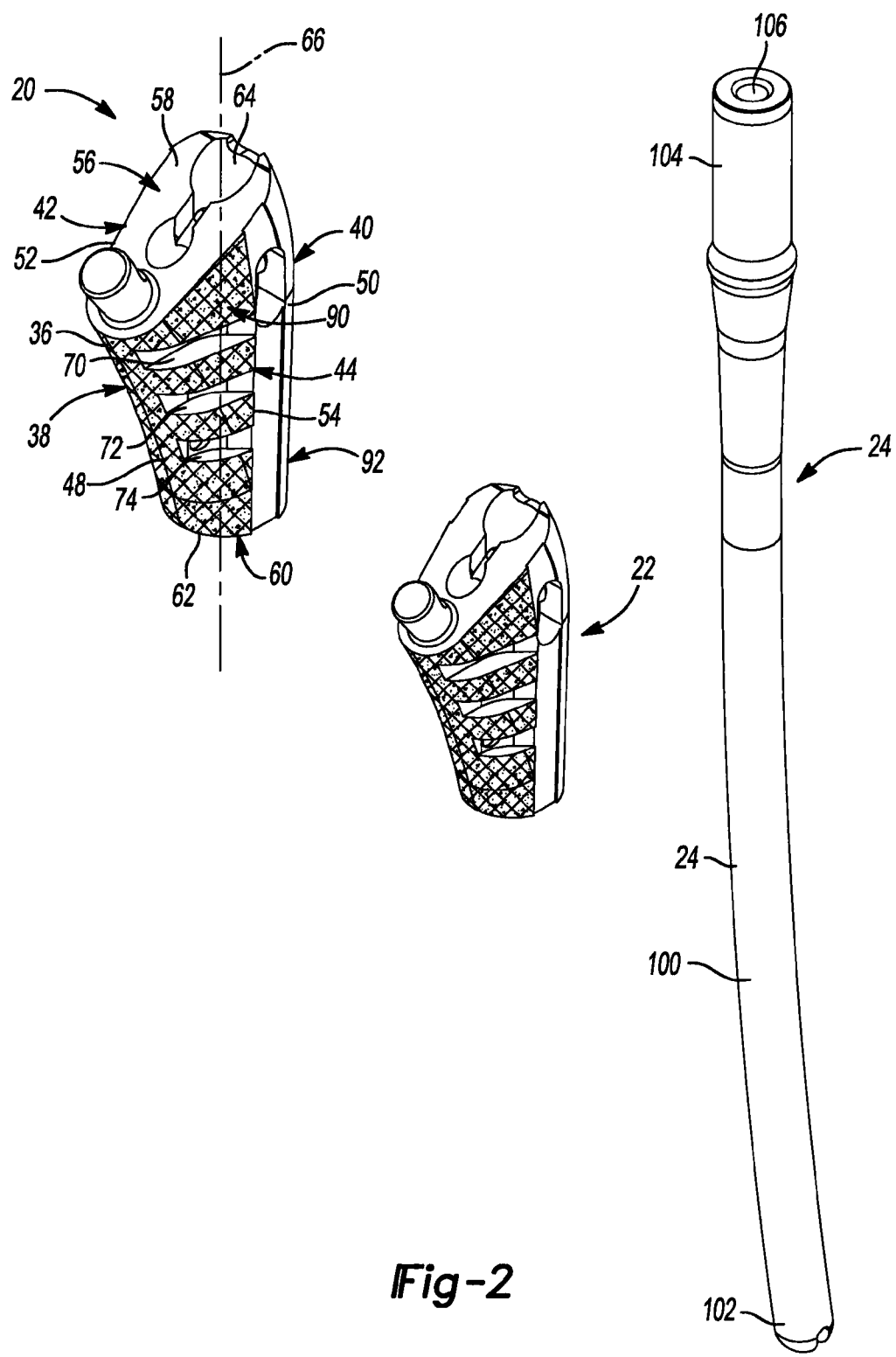
FIG. 2 is a perspective view of a first and a second broach that are selectively and alternatively used with an exemplary stem according to the present teachings.

With initial reference to FIG. 1, a revision system for preparing a proximal femur in accordance to one example of the present teachings is shown and generally identified at reference numeral 10. The revision system 10 can generally comprise a broach system assembly 12, a cutting scribe assembly 14, a cutting guide assembly 16 and a proximal femoral implant 18. In one example, the broach system assembly 12 can comprise a collection of broaches, such as, but not limited to, a first broach 20, a second broach 22, a broach handle 13, a stem 24 and a shelf insert 26.

As will become appreciated from the following discussion that the broach system assembly 12 can be used to broach a proximal femur 30 (FIG. 4) subsequent to a preliminary proximal femur preparation step, such as reaming an intramedullary (IM) canal 32 of the proximal femur 30. In the exemplary drawings, the first broach 20 is larger than the second broach 22 with the understanding that several broaches may be included having successively larger and/or smaller sizes for progressively broaching the proximal femur 30 in successively larger areas as needed. The cutting scribe assembly and the cutting guide assembly 14 and 16, respectively, can be selectively and alternatively used for locating and assisting in the preparation of the cuts prepared in the proximal femur 30 for receipt of a desired implant, such as the proximal femoral implant 18 discussed herein. Once the proximal femur 30 has been cut, the first broach 20 (or second broach 22, etc.) can be coupled to the stem and trialed.

With continued reference to FIG. 1 and additional reference now to FIGS. 2-5, the first broach 20 will be further described. It will be appreciated that the second broach 22 will be constructed similarly. Therefore, only specific description of the first broach 20 will be expressly described herein. The first broach 20 includes a broach body 36 that generally includes a medial side 38, a lateral side 40, a posterior side 42 and an anterior side 44. The context of the respective sides is described as they would be identified when the first broach 20 is used in a left femur. As will become appreciated from the following discussion, the same first broach 20 can be used with a right femur with identification of the anterior and posterior sides being reversed.

The medial side 38 can have a medial surface 48. The lateral side 40 can have a lateral surface 50. The posterior side 42 can have a posterior surface 52. The anterior side 44 can have an anterior surface 54. The broach body 36 can also include a superior side 56 having a superior surface 58 and an inferior side 60 having an inferior surface 62. A proximal locating bore 64 can be provided on the superior surface 58 of the superior side 56. The broach body 36 can define a longitudinal axis 66. In one example, the longitudinal axis 66 can coincide with the center of the proximal locating bore 64.

A first, second and third pair of notches 70, 72 and 74, respectively are provided on the broach body 36 (FIG. 3). The first, second and third pairs of notches 70, 72 and 74 can further include a first, second and third pair of insets 76, 78 and 80, respectively. In one example, the first, second and third pairs of notches 70, 72 and 74, respectively can be provided in the broach body 36 at the medial side 38, the posterior side 42, and the anterior side 44. Each notch of each pair of notches 70, 72 and 74 are disconnected from its corresponding notch so as to form a first, second and third pair of opposing surfaces 84, 86 and 88 (FIG. 3). The notches 70, 72 and 74 can be used to selectively accept the shelf insert 26 as will be further described.

The broach body 36 can include a roughened cutting surface 90. In one example, the roughened cutting surface 90 can include a ground cutting teeth. The broach body 36 can further include a smooth, non-cutting surface 92. The roughened cutting surface 90 can be provided on the medial side 38 and portions of both of the posterior side 42 and anterior side 44. The smooth, non-cutting surface 92 can be provided on the lateral side 40 and portions of both of the posterior side 42 and anterior side 44. The inferior surface 62 of the inferior side 60 can define a bore 95 having a female receiving taper 96 (FIG. 4).

The stem 24 can generally include a longitudinal body 100 including a distal end 102 and a proximal end 104. The proximal end 104 can be received in the female receiving taper 96 provided in the broach body 36. A threaded aperture 106 can be provided on the proximal end 104 of the stem 24, such as for receiving a fastener, such as a bolt (not specifically shown) that is located into the proximal locating bore 64 of the broach body 36. In one example, the body 100 of the stem 24 can be slightly curved for locating into a similarly curved IM canal 32 of the proximal femur 30. The stem 24 can be coupled to the first broach 20 to assist in locating into the IM canal of the femur 30, such as during broaching, used with the cutting scribe assembly 14, used with the cutting guide assembly 16 and trialing.

With specific reference now to FIGS. 1, 19 and 20, the shelf insert 26 will be further described. The shelf insert 26 can be used with the first broach 20 during trialing to reference a location of a femoral ledge 108 (FIG. 19) for estimation of an implanted location (and size) of a calcar shelf of the proximal femoral implant 18. The shelf insert 26 can generally include a shelf body 110 that is generally in the form of a U-shape. The shelf body 110 can include a first finger 112 and a second finger 114 provided on opposite ends of a central connecting portion 116. A first and a second protrusion 118 and 120, respectively, are provided on the first and second fingers 112 and 114. In general, and as will be described in greater detail herein, the first and second fingers 112 and 114 are configured to selectively and alternatively locate into one of the first, second or third pairs of notches 70, 72 and 74 on the broach body 36. The protrusions 118 and 120 are configured to operatively nest into one of the first, second or third pairs of insets 76, 78 or 80 provided on the respective pairs of notches 70, 72 and 74, respectively. The interaction of the first and second protrusions 118 and 120 with the respective pairs of insets 76, 78 and 80 can provide a positive locating interaction of the shelf insert 26 into the particular pair of notches 70, 72 and 74.

Additionally, the slidable translation of the first and second protrusions 118 and 120 along the respective opposing surfaces 84, 86 or 88 followed by positive location of the first and second protrusions 118 and 120 into the first, second or third pairs of insets 76, 78 and 80 can provide a user tactile feedback that the shelf insert 26 is positively located in an assembled position with the desired pair of notches 70, 72 or 74. In one example, the body 110 can be compliant to allow for marginal flexing outwardly of the first and second fingers 112 and 114 during slidable translation of the first and second protrusion 118 and 120 across the opposing surfaces 84, 86 or 88.

Figure 8:
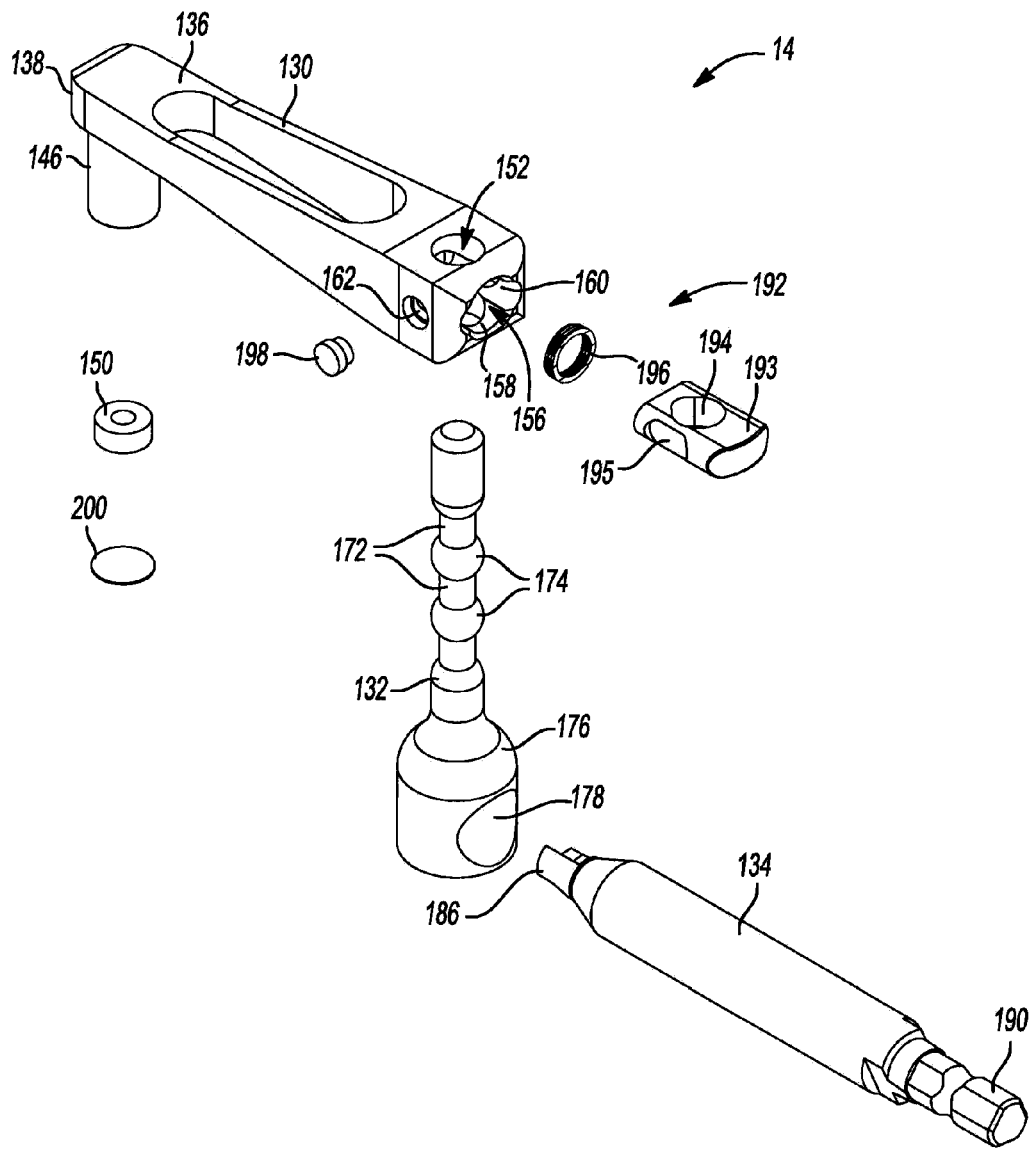
FIG. 8 is an exploded perspective view of the scribe assembly of FIG. 5.

With reference now to FIGS. 1 and 5-12, the cutting scribe assembly 14 according to one example of the present teachings will be described. The cutting scribe assembly 14 can generally comprise an arm 130, a connecting link 132 and a cutting tool 134. The arm 130 can include an arm body 136 having a first end 138 and a second end 140. The arm body 136 can generally extend along a longitudinal axis 144. The first end 138 of the arm 130 can include a locating boss 146 that extends along a boss axis 148. A magnet 150 can be disposed in the locating boss 146. The second end 140 can include a connecting link opening 152 defined along a connecting link opening axis 154. According to one example, the boss axis 148 and the connecting link opening axis 154 can be parallel relative to each other and perpendicular relative to the longitudinal axis 144 of the arm 130. As best illustrated in FIG. 8, the second end 140 can also include a fixing assembly opening 156. The fixing assembly opening 156 can generally include a first sidewall 158 and a second sidewall 160. In one example, the first sidewall 158 can be generally cylindrical while the second sidewall 160 can be generally in the form of an oval. A peg hole 162 can be provided in the second end 140 of the arm 130.

The connecting link 132 can generally include a connecting link body 166 having a first end 168 and a second end 170. The connecting link body 166 can include a series of alternating narrow portions 172 and bulbous portions 174. The second end 170 can include a guiding body 176 that includes a passage 178 therethrough.

The cutting tool 134 can generally include a cutting tool body 180 (FIG. 5) that extends along a longitudinal axis 182. The cutting tool body 180 can generally include a first end 184 having a cutting tip 186 and a second end 188 having a tool engaging end 190.

With particular reference now to FIG. 8, the cutting scribe assembly 14 can also include a fixing assembly 192 that includes a fixing insert 193, a spring 196 and a peg 198. The fixing insert 193 can include an insert opening 194 and a slide surface 195. The magnet 150 can be secured into the locating boss 146 by a securing washer 200.

One example of assembling the cutting scribe assembly 14 according to the present teachings will be described. Assembly of the cutting scribe assembly 14 can be conducted prior to, subsequent to or concurrently with connecting the cutting scribe assembly 14 to the first broach 20. Furthermore, the particular sequence of assembly discussed herein in relation to the cutting scribe assembly 14 or other assemblies of this disclosure is merely exemplary and does not denote a specific order of steps. At the outset, the connecting link 132 can be located through the connecting link opening 152 of the arm 130. In one example, the first end 168 can be advanced through the connecting link opening 152. Insertion of the connecting link 132 through the connecting link opening 152 can concurrently include passing the first end 168 of the connecting link 132 through the insert opening 194 of the fixing insert 193. Interaction of the fixing insert 193 and the spring 196 against the connecting link 132 can facilitate locating the connecting link 132 at a desired narrow portion 172. Sequential advancement of the connecting link 132 through the connecting link opening 152 of the arm 130 will cause the peg 198 to ride along the slide surface 195 of the fixing insert 193 during advancement over the bulbous portions 174 to one of a plurality of discreet positions.

Figure 5:
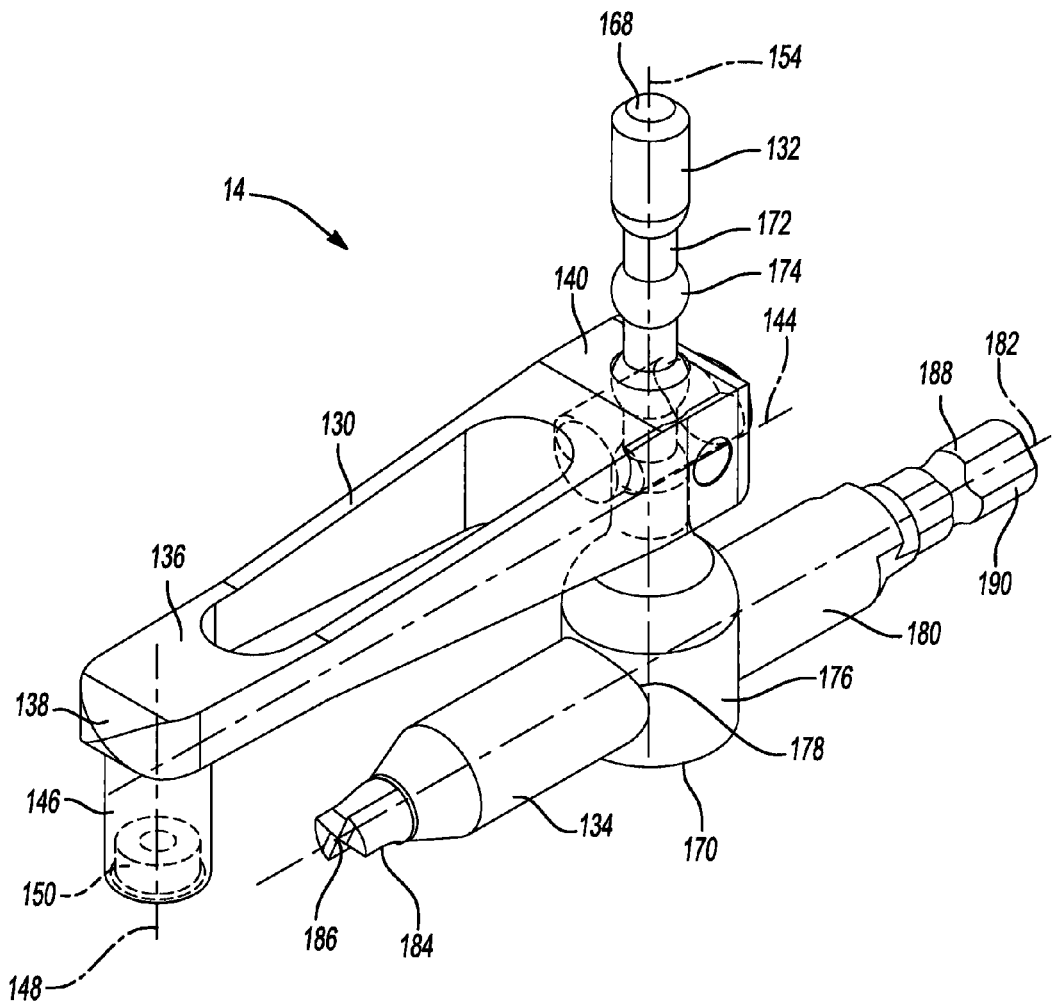
FIG. 5 is a front perspective view of a cutting scribe assembly according to the present teachings.
Figure 6:
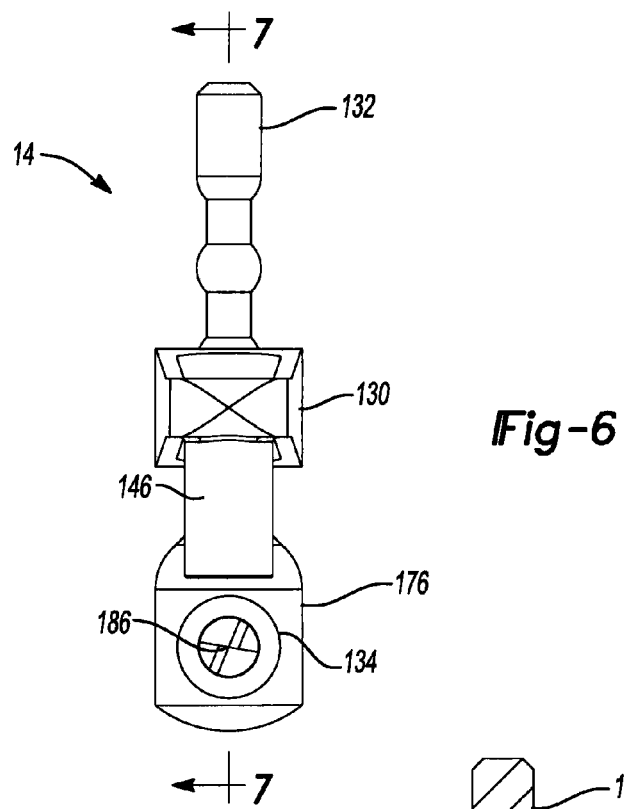
FIG. 6 is a front perspective view of the scribe assembly of FIG. 5.
Figure 7:
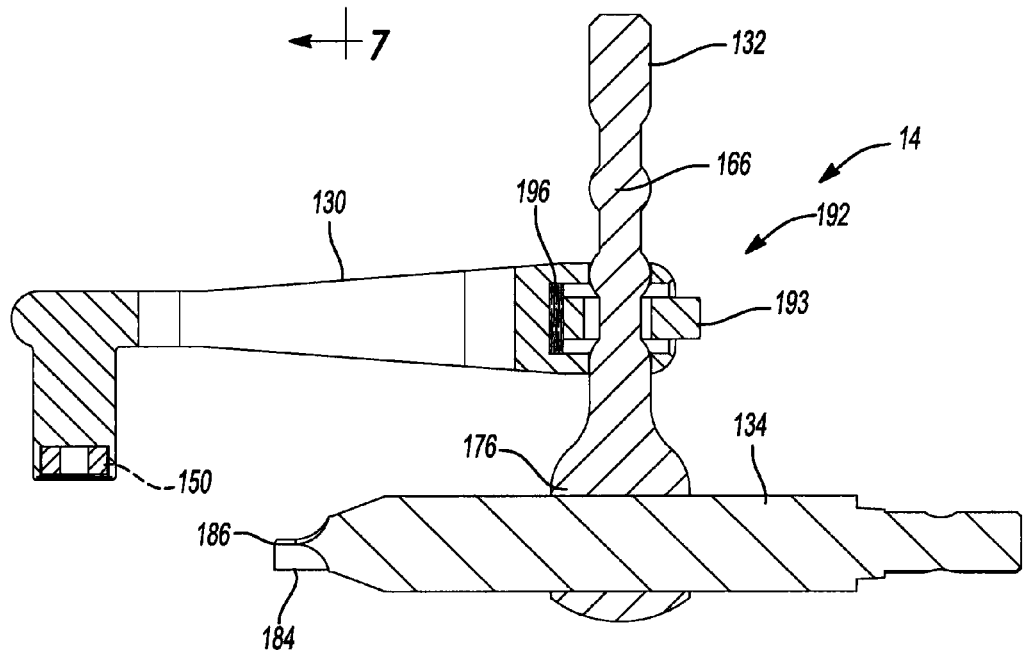
FIG. 7 is a sectional view of the scribe assembly taken along lines 7-7 of FIG. 6.

Once assembled, the longitudinal axis 182 of the cutting tool 134 can have a parallel relationship to the longitudinal axis 144 of the arm 130 (FIG. 5). Additionally, the longitudinal axis 182 of the cutting tool 134 can be perpendicular to the link opening axis 154 and a longitudinal axis of the connecting link 132. The cutting tool 134 can be slidably advanced through the passage 178 in the guiding body 176 of the connecting link 132. It is appreciated that the cutting tool 134 can locate at a plurality of locations relative to the passage 178 along the longitudinal axis 182. The cutting tool 134 can be rotatably driven such as by a drill coupled to the tool engaging end 190 to score and/or cut into the bone 30 at the desired location.

Figure 13:
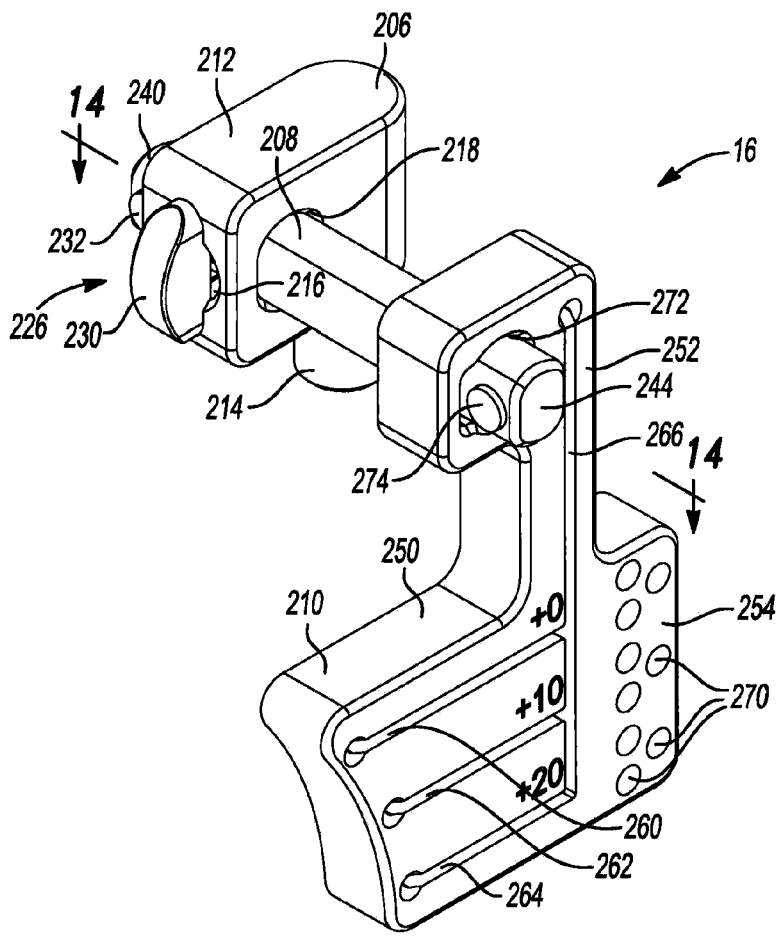
FIG. 13 is a perspective view of a cutting block assembly according to one example of the present teachings.
Figure 14:
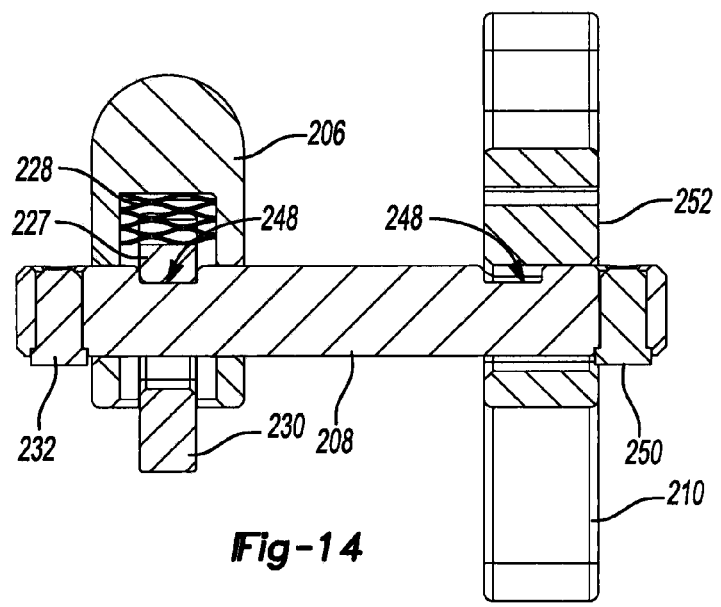
FIG. 14 is a sectional view of the cutting block assembly taken along lines 14-14 of FIG. 13.
Figure 15:
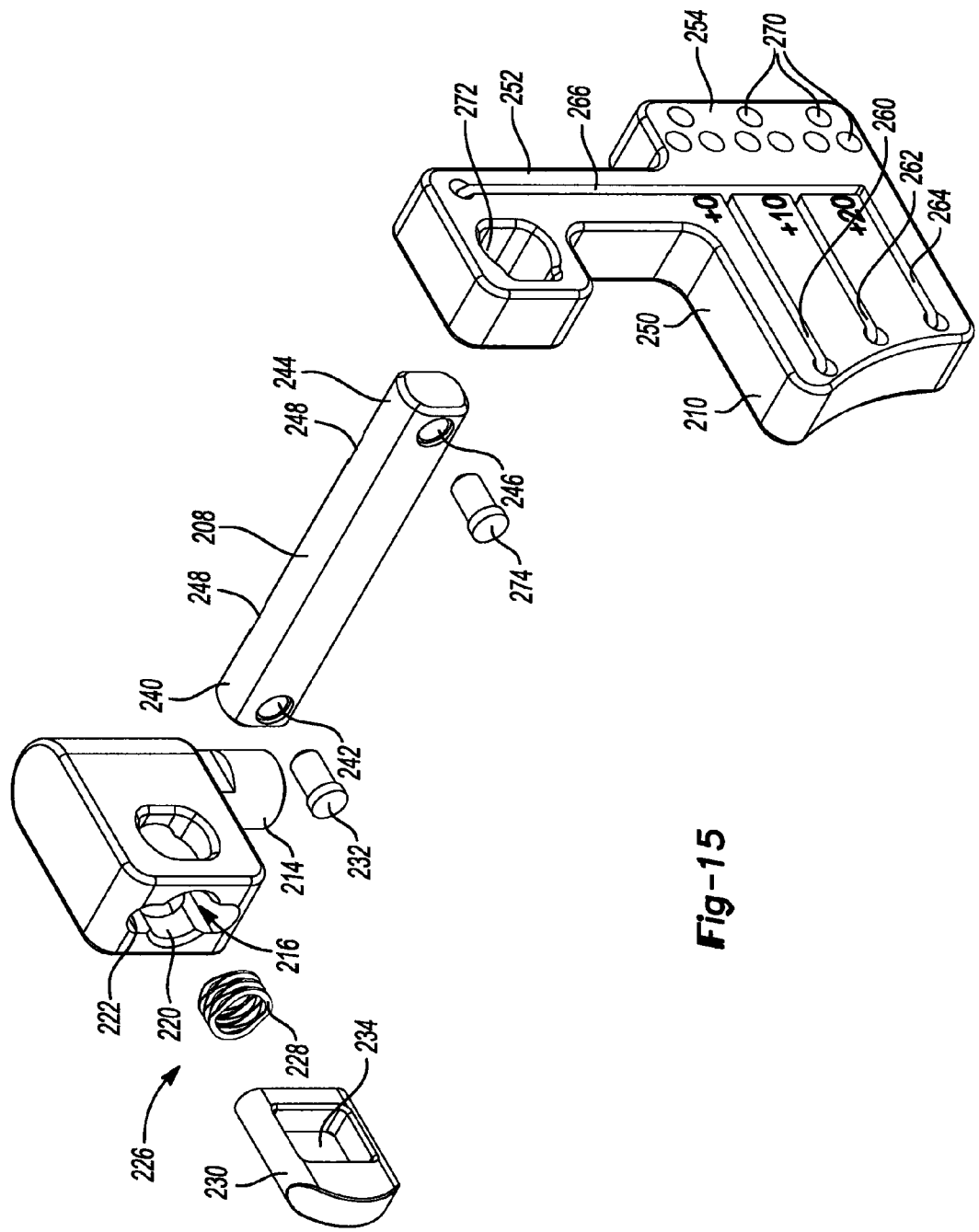
FIG. 15 is an exploded perspective view of the cutting block assembly of FIG. 13.

With reference now to FIGS. 1 and 13-18, the cutting guide assembly 16 according to one example of the present teachings will be described. With initial reference to FIG. 16, the cutting guide assembly 16 can include an arm 206, a connecting link 208 and a cut block 210. The arm 206 can include an arm body 212 that has a locating boss 214, a fixing assembly opening 216 (FIG. 15) and an arm passage 218 (FIG. 13). The fixing assembly opening 216 can include a first sidewall 220 and a second sidewall 222. The first sidewall 220 can generally be in the form of a cylinder while the second sidewall 222 can generally be in the form of an oval. The fixing assembly opening 216 can be configured for receipt of a fixing assembly 226 that includes a tang 227 (FIG. 14), a spring 228, a key 230 and a peg 232. The key 230 can include a key opening 234 (FIG. 15).

The connecting link 208 can include a first end 240 having a first peg opening 242 and a second end 244 having a second peg opening 246. The connecting link 208 can have a longitudinal body having a substantially oval cross-section. The connecting link can have a depression 248 formed on opposite ends.

The cut block 210 can generally include a block body 250 having a longitudinal body portion 252 and an alignment body portion 254 (FIG. 13). The block body 250 can include a first, second, third and fourth cut slot 260, 262, 264 and 266, respectively. The first, second and third cut slots 260, 262 and 264 can be configured generally parallel relative to each other and transverse to the fourth cut slot 266. A plurality of pin holes 270 can be formed through the alignment body portion 254 of the cut block 210 for selectively pinning the cut block 210 in the event it is desired to remove the connecting link 208 and arm 206. A block passage 272 can be formed through the block body 250 for receipt of the second end 244 of the connecting link 208. A peg 274 can cooperate with the second peg opening 246 to capture the cut block 210 at the second end 244 of the connecting link 208 in an assembled position.

The proximal femoral implant 18 can include a body 276 having an inferior coupling portion 278, a projection 280, a superior opening 281 and a calcar shelf portion 282. The features of the proximal femoral implant 18 are merely exemplary. The shape and profile can substantially correspond to the shape and profile of the first broach 20, second broach 22, etc. It is further appreciated that a plurality of different sized proximal femoral implants may be provided to correspond to given needs of a particular patient. The shelf insert 26 can engage a calcar portion of the proximal femur 30 to simulate the ultimate location of the calcar shelf portion 282 of the proximal femoral implant 18 once implanted.

Assembly of the cutting guide assembly 16 according to one example will now be described. It is appreciated that assembly of the cutting guide assembly 16 can be carried out prior to, subsequent to or during assembly of the cutting guide assembly 16 to the first broach 20. Initially, the first end 240 of the connecting link 208 can be advanced through the arm passage 218. Advancement of the first end 240 of the connecting link 208 through the arm passage 218 can concurrently include passage of the first end 240 of the connecting link 208 through the key opening 234 in the key 230. The tang 227 can be biased by the spring 228 into nesting engagement with a depression 248 (FIG. 14) provided on the first end 240 of the connecting link 208. In one example, the peg 232 can then be advanced through the first peg opening 242 to secure the position of the arm body 212 to the first end 240 of the connecting link 208. The cut block 210 can then be coupled relative to the connecting link 208. In one example, the second end 244 of the connecting link 208 can be slidably advanced through the block passage 272. The peg 274 can then be located through the second peg opening 246 to position the cut block 210 relative to the second end 244 of the connecting link 208. It is appreciated that while the cutting guide assembly 16 is shown in the drawings for cooperation with a left femur, that the cutting link 208 and the cut block 210 can alternatively be assembled to extend through the opposite side of the arm passage 218 of the arm 206 for cooperation with a right femur.

An exemplary method of preparing a proximal femur 30 according to the present teachings will now be described. At the outset, the proximal femur 30 is first prepared, such as by reaming the IM canal 32 of the proximal femur 30. In one example, the IM canal 32 of the proximal femur 30 can be reamed using a modular reamer assembly, such as in currently pending and commonly owned U.S. patent application Ser. No. 12/502,833, entitled "Modular Reaming System for Femoral Revision". The contents of this application are expressly incorporated herein by reference.

According to some examples, successive reamers may be used having progressively larger sizes for initially preparing the proximal femur 30. Reaming of the proximal femur 30 along the IM canal 32 prepares the proximal opening on the lateral side of the proximal femur 30. As can be appreciated, the trochanter of the proximal femur 30 is relatively fragile and it can be desirable to impart minimal broaching action in the proximal femur 30 along the IM canal 32. As discussed above, the first broach 20 includes a lateral side 40 that has a smooth surface 92, such that if further preparation of the proximal femur 30 is desired, advancement of the first broach 20 (and other broaches of the broach system assembly 12) will only cause a cutting action along the roughened, cutting surface 90 on the medial surface 48 of the broach body 36. In this way, slidable advancement of the smooth surface 92 on the lateral side 40 of the broach body 36 will not transfer any unnecessary forces along the lateral side of the proximal femur 30 reducing the likelihood of damage and/or fracture of the proximal femur 30 at the lateral side. In some examples where the proximal femur 30 is particularly deficient such as at the medial side, the shelf insert 26 may be located at one of the pair of notches 70, 72 and 74 to further assist in proper alignment. The broach handle 13 may be coupled to the first broach 20 during broaching.

Once the proper sized broach (first broach 20, second broach 22, etc.) has been verified at the proximal femur 30, the cutting scribe assembly 14 or the cutting guide assembly 16 can be coupled to the proximal locating bore 62 of the broach body 36. Again, either the cutting scribe assembly 14 or the cutting guide assembly 16 can be utilized for identifying the desired cut locations on the proximal femur 30 that will correspond to the profile of the proximal femoral implant 18.

Figure 9:
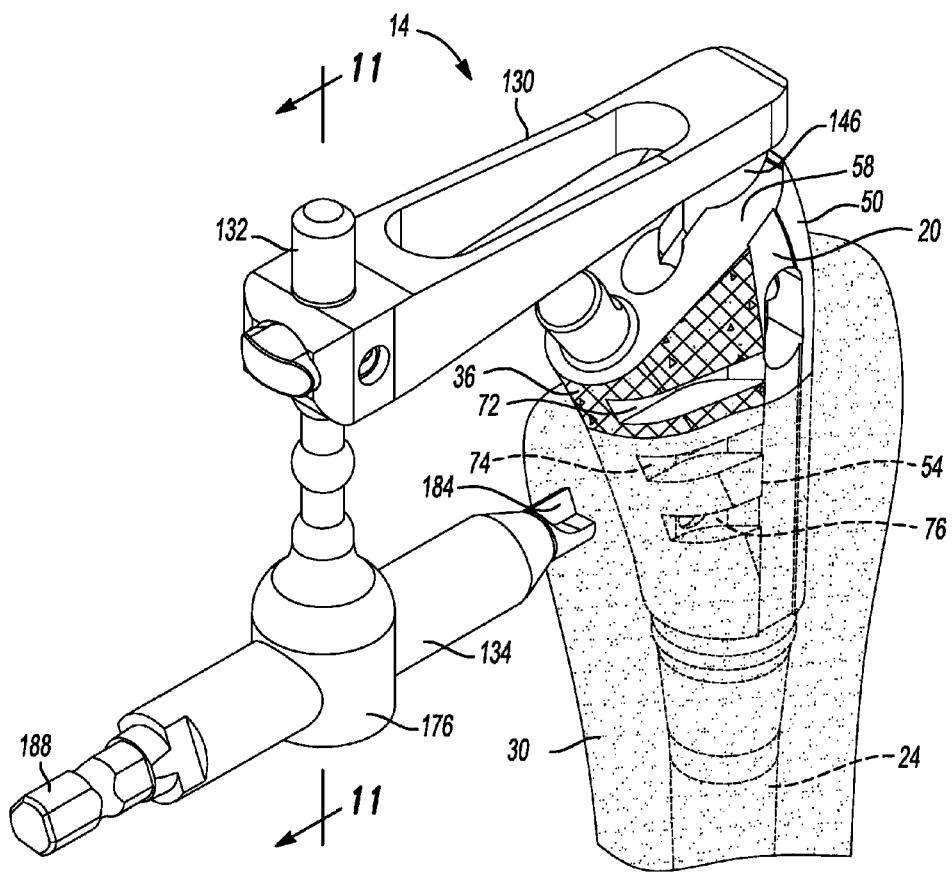
FIG. 9 is a medial perspective view of an exemplary left proximal femur shown with the scribe assembly and first broach.
Figure 12:
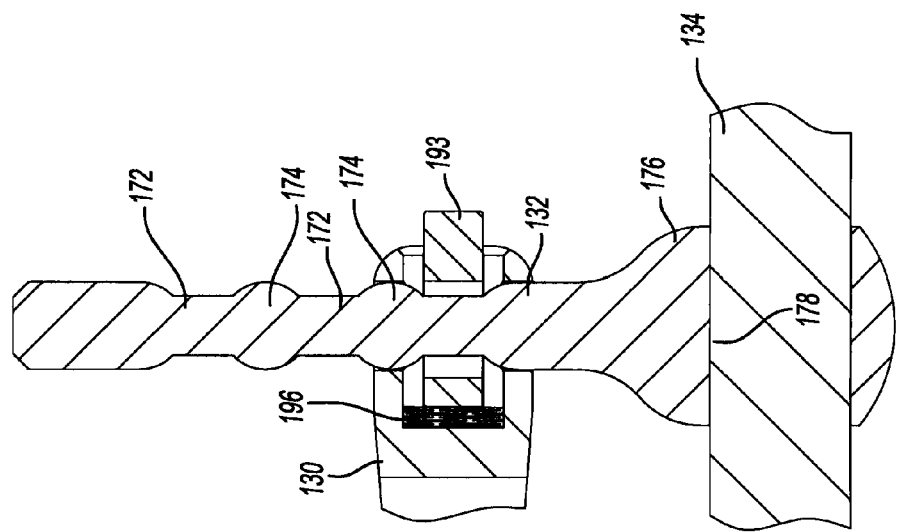
FIGS. 11 and 12 are exemplary sectional views of the scribe assembly taken along lines 11-11 of FIG. 9 illustrating various locations of adjustment along a connecting link of the scribe assembly.
Figure 11:
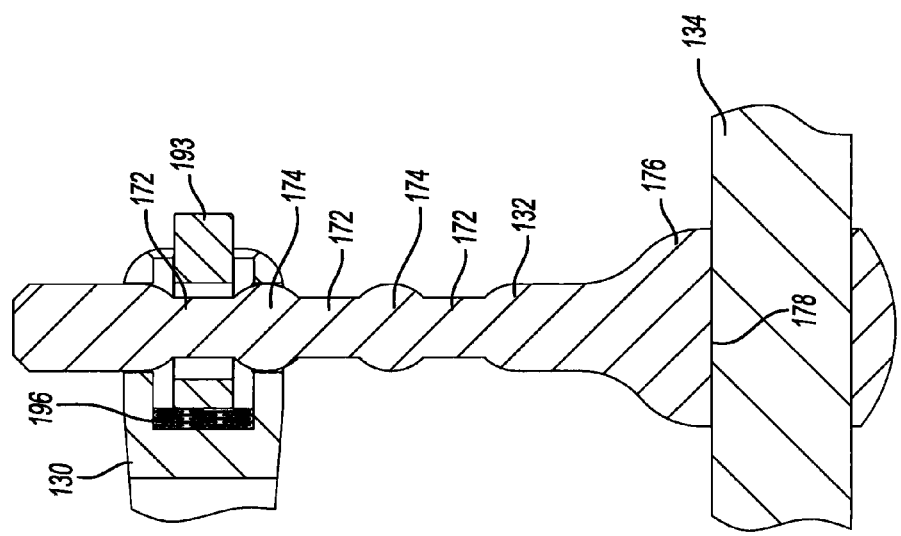

With initial reference now to FIGS. 9 and 10, selection of the cutting scribe assembly 14 and its use will be described. At the outset, the surgeon can insert the locating boss 146 into the proximal locating bore 64 (see also FIG. 2). The magnet 150 can be magnetically attracted to the metallic properties of the broach body 36, such that the locating boss 146 is coupled to the broach body 36, but still is allowed to rotate around the boss axis 148. Next, the surgeon inspects the condition of the proximal femur 30 and identifies the deficient femoral bone. The connecting link 132 can be raised or lowered through the connecting link opening 152 until the cutting tip 186 of the cutting tool 134 is located just below the deficient bone.

In one example, the arm 130 can be rotated around the boss axis 148 (FIG. 10), such that the cutting tip 186 can scribe or make a mark 285 on the proximal femur 30 at any location along the medial side of the proximal femur 30. In one example, a tool, such as a rotary tool (not specifically shown) can be coupled to the tool engaging end 190 of the cutting tool 134. The tool can impart rotational motion of the cutting tool 134 around its longitudinal axis 182 causing the cutting tip 186 to partially drill or score the identified area of the proximal femur 30. Once the femur has been sufficiently scored, the cutting scribe assembly 14 along with the broach body 36 can be removed from the proximal femur 30. The proximal femur then can be cut in an L-shaped pattern to match the profile of the proximal femoral implant 18 according to conventional methods.

Figure 16:
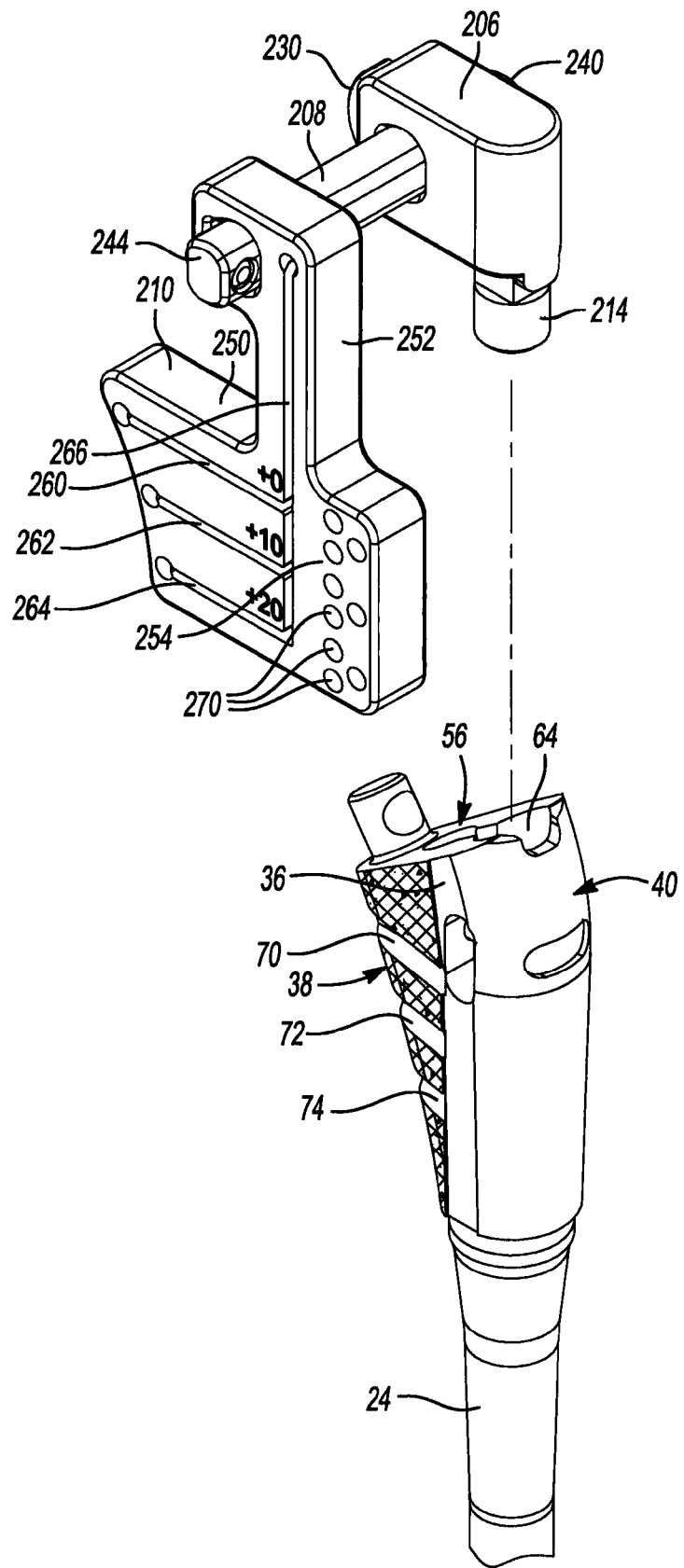
FIG. 16 is an exemplary exploded lateral assembly view of the cutting block assembly shown during assembly of the cutting block with the first broach.
Figure 17:
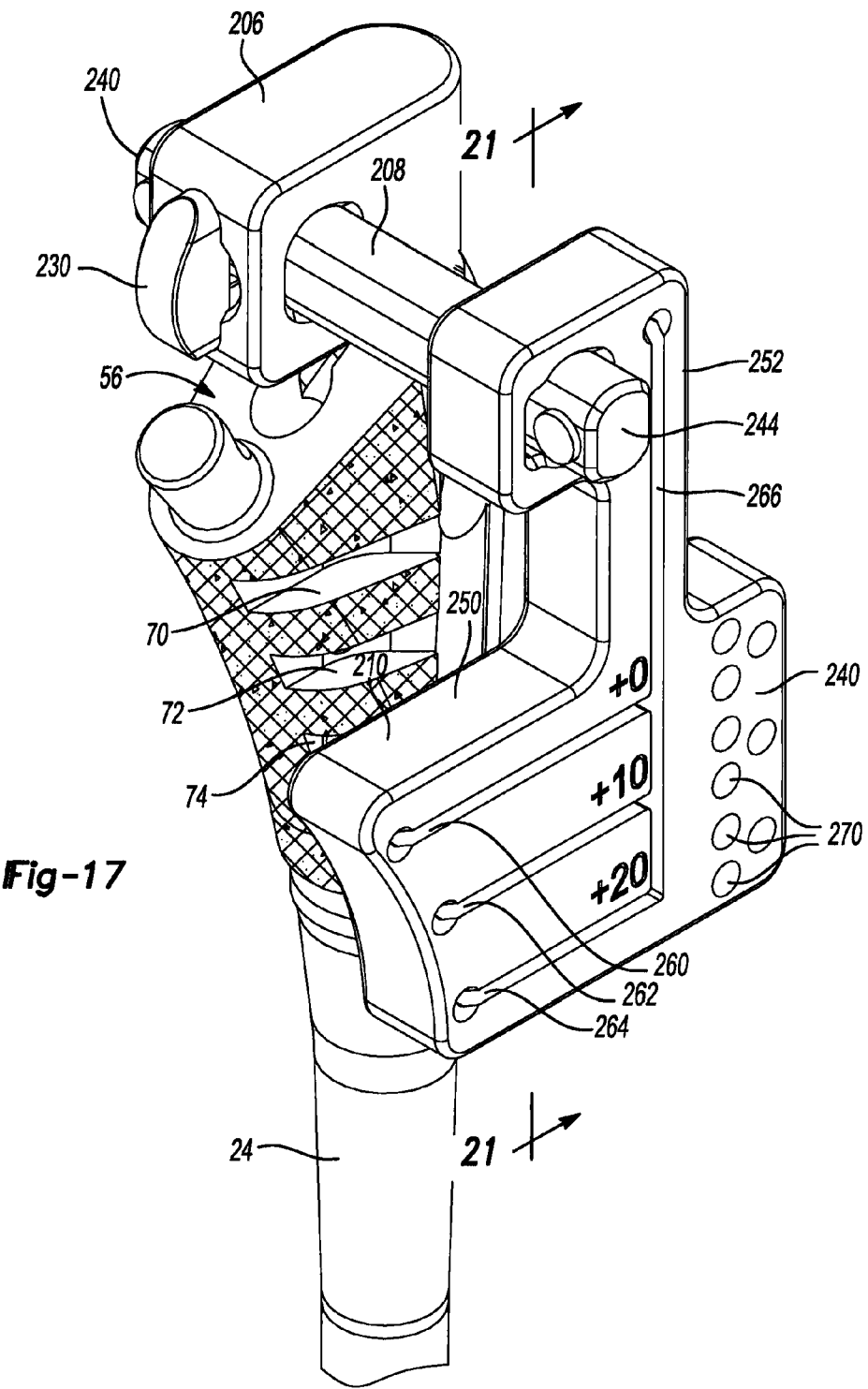
FIG. 17 is a perspective view of the cutting block assembly and first broach in an assembled position.
Figure 18:
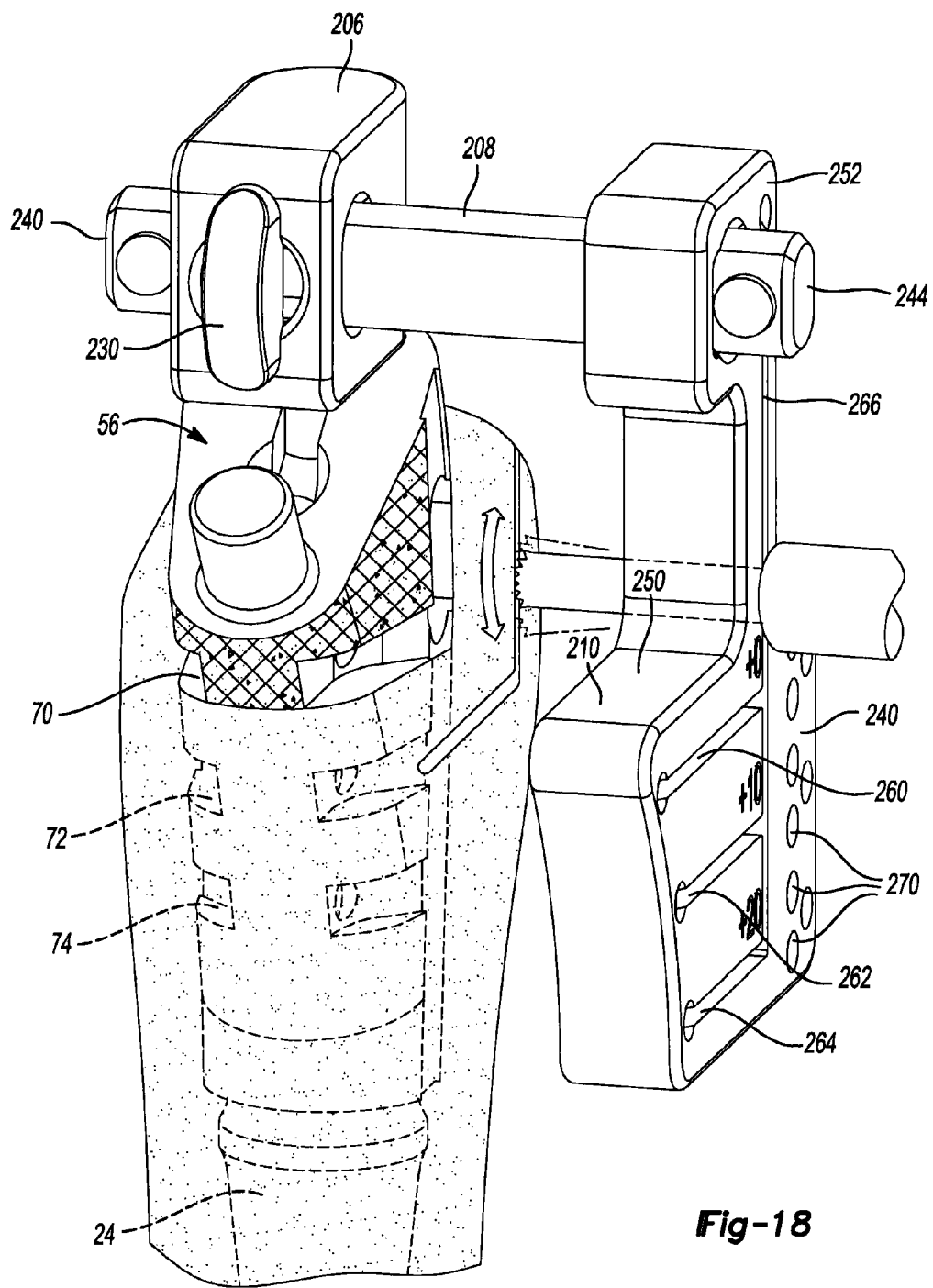
FIG. 18 is a medial perspective view of an exemplary left proximal femur shown with an exemplary cutting instrument cooperating with the cutting block assembly.

Alternatively, selection and use of the cutting guide assembly 16 will now be described with specific reference to FIGS. 16-18. At the outset, the locating boss 214 of the arm body 212 is located into the proximal locating bore 64 of the broach body 36. Next, the surgeon can assess the condition of the proximal femur. If it is determined that the proximal femur includes areas that are sufficiently deficient, the surgeon can determine that a proximal femoral implant 18 having a calcar shelf portion 282 is desired. Next, the surgeon can identify the desired level of resection needed in view of the condition of the proximal femur 30. The surgeon can then make a partial cut (FIG. 18) through one of the first, second or third cutting slots 260, 262 or 264 in the block body 250 at the desired height. Additionally, a partial cut can be made through the fourth cut slot 266.

According to one example, once partial cuts have been marked into the proximal femur, the entire cutting block assembly 16 and the broach body 36 can be removed from the proximal femur. The L-shaped cut can then be carried out. In another example, the alignment body portion 254 can be pinned to the proximal femur 30 through the pin holes 270 and the remainder of the cutting guide assembly (the arm 206 and the connecting link 208) is removed together with the broach body. The L-shaped cut can be completed with the alignment body portion 254 still located on the proximal femur 30.

Figure 22:
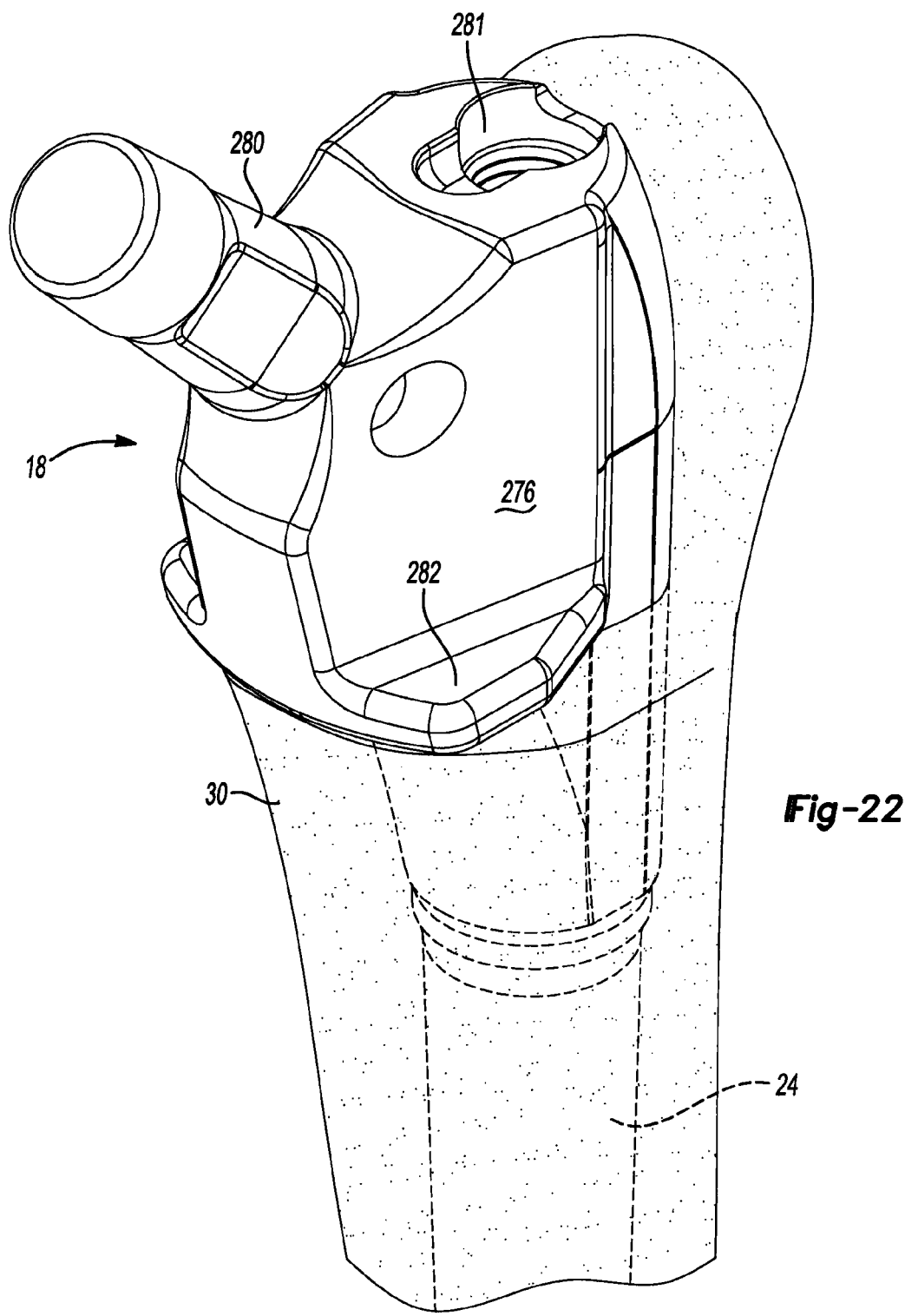
FIG. 22 is an anterior perspective view of the proximal femoral implant located into an IM canal of the prepared left proximal femur.

Once the proximal femur 30 has been prepared, the proximal femoral implant 18 (FIGS. 21 and 22) can be advanced into the prepared proximal femur 30. A desired fit can be verified by the surgeon.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for preparing a proximal femoral implant for a proximal femoral prosthesis, the system comprising:
    a member configured to be placed in a proximal femur, the member having a femur cutting surface for preparing the proximal femur, the member having a plurality of notches formed into the member; and
    a shelf body configured to selectively engage at least one notch of the plurality of notches formed into the member to estimate a location of a calcar shelf during trialing and preparing the proximal femur;
    wherein the shelf body is configured to removably engage the member;
    wherein the shelf body is about a U-shape that comprises a first finger, a second finger, and a central connecting portion;
    wherein each of the first finger and the second finger both taper away from the central connecting portion; and
    wherein the central connecting portion is configured to extend beyond a femoral ledge of the femur when the shelf body is engaged with the at least one notch in the member.

2. The system of claim 1 wherein the finger and the second finger are on opposite ends of the central connecting portion.

3. The system of claim 1 wherein a first protrusion is provided on the first finger and a second protrusion is provided on the second finger to provide a positive locating interaction of the shelf body into the at least one notch.

4. The system of claim 3, wherein the first protrusion and the second protrusion are configured to provide a tactile feedback that the shelf body is positively located in an assembled position with the at least one notch.

5. The system of claim 4 wherein the shelf body is compliant to allow for flexing outwardly of the first finger and the second finger during slidable translation of the first protrusion and the second protrusion across opposing surfaces.

6. The system of claim 3, wherein each notch of the plurality of notches is a pair of notches.

7. The system of claim 6 wherein the first finger and the second finger are configured to selectively and alternatively locate into one of a first, second or third pairs of notches on the member.

8. The system of claim 7 wherein each pair of notches of the plurality of notches are axially spaced apart on the member.

9. The system of claim 1, further comprising:
    a proximal femoral implant having a calcar shelf
    wherein the member is a broach member configured to be placed in the proximal femur and removed once the proximal femur is prepared for the proximal femoral implant having the calcar shelf.

10. The system of claim 9, further comprising:
    a stem having a first terminal end configured to be positioned within a portion of the femur distal to the proximal femur and a second terminal end having a male taper configured to be adjacent to the proximal femur;
    wherein the broach member includes a bore to engage the male taper of the stem;
    wherein the proximal femoral implant includes a portion to engage the male taper of the stem;

wherein a shape and profile of the proximal femoral implant corresponds to a shape and profile of the broach member.

11. The system of claim 9, wherein the broach member includes a proximal locating bore on a superior surface of a superior side of the broach member;
   wherein the broach member has a longitudinal axis that coincides with a center of the proximal locating bore;
   wherein the proximal locating bore is configure to receive at least one of a locating boss of a cutting scribe or a locating boss of a cutting assembly.

12. The system of claim 1, wherein the member comprises:
   a distal end surface;
   a proximal end surface;
   a medial side surface extending between the distal end surface and the proximal end surface, the medial side surface being roughened to form the cutting surface;
   a lateral side surface extending between the distal end surface and the proximal end surface, the lateral side surface being smooth.

13. A system for preparing a proximal femoral implant for a proximal femoral prosthesis, the system comprising:
   a member configured to be placed in a proximal femur, the member having a medial side with a medial surface that is roughened to cut the proximal femur and a lateral side with a lateral surface that is a smooth, non-cutting surface;
   a shelf insert that is about U-shaped and removably engages at least one pair of notches formed into the member;
   wherein the shelf insert has a plurality of lateral fingers and a connecting medial portion of a resilient material;
   wherein at least a first lateral finger of the plurality of lateral fingers engages a first notch of the at least one pair of notches and at least a second lateral finger of the plurality of lateral fingers engages a second notch of the at least one pair of notches;
   wherein each lateral finger of the plurality of lateral fingers is distally tapered; wherein the shelf insert is sized to extend beyond an outer surface of the proximal femur when the shelf insert is engaged with the at least one pair of notches formed into the member.

14. The system of claim 13, wherein the plurality of lateral fingers includes a first finger having a first proximate end and a second finger having a second proximate end, wherein the first proximate end and the second proximate end are connected together at the connecting medial portion and at least the first proximate end is narrower than a distal end of the first finger.

15. The system of claim 14, wherein the at least one pair of notches formed into the member includes a plurality of pairs of notches formed into the member, wherein each of the at least one pair of notches formed into the member is axially spaced along the member.

16. A system for preparing a proximal femur for a proximal femoral prosthesis, the system comprising:
   a broach member configured to prepare the proximal femur, the broach member having at least a first distal end surface configured to be placed inside the femur spaced from the proximal femur and a second proximal end surface configured to be placed outside the proximal femur, wherein the broach member includes at least a medial femur cutting surface disposed between the first distal end surface and the second proximal end surface and a lateral femur smooth surface disposed between the first distal end surface and the second proximal end surface, wherein a plurality of pairs of notches are spaced along a length of the medial femur cutting surface of the broach member; and
   a shelf insert configured to be selectively located on the broach member in at least one pair of notches of the plurality of pairs of notches;
   wherein the shelf insert includes a first arm configured to be inserted into a first notch of at least one pair of notches and a second arm configured to be inserted into a second notch of the at least one pair of notches and the first arm and the second arm are connected at a connection region;
   wherein the first arm and the second arm are both tapered away from the connection region;
   wherein the first arm includes a first protrusion that extends from a surface of the first arm; wherein at least one notch of the at least one pair of notches includes an inset to receive the first protrusion; wherein the shelf insert is further configured to engage a calcar portion of the proximal femur when connected in at least one selected pair of notches of the plurality of pairs notches to simulate an ultimate location of a calcar shelf portion of a proximal femoral implant once implanted; wherein the proximal femoral implant is separate from the broach member; wherein the shelf insert extends beyond the medial femur cutting surface of the broach member and a calcar shelf of the calcar portion of the proximal femur when fully connected in the at least one selected pair of notches.

* * * * *